(12) United States Patent
Rezai et al.

(10) Patent No.: US 7,477,945 B2
(45) Date of Patent: Jan. 13, 2009

(54) DELIVERY DEVICE FOR STIMULATING THE SYMPATHETIC NERVE CHAIN

(75) Inventors: Ali Rezai, Bratenhal, OH (US); Thomas MacMartin Harman, II, Palo Alto, CA (US); Ashwini Sharan, Mt. Laurel, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 175 days.

(21) Appl. No.: 10/502,347

(22) PCT Filed: Feb. 3, 2003

(86) PCT No.: PCT/US03/03003

§ 371 (c)(1),
(2), (4) Date: Jul. 14, 2005

(87) PCT Pub. No.: WO03/063692

PCT Pub. Date: Aug. 7, 2003

(65) Prior Publication Data

US 2006/0155344 A1 Jul. 13, 2006

Related U.S. Application Data

(60) Provisional application No. 60/353,700, filed on Feb. 1, 2002.

(51) Int. Cl.
*A61N 1/00* (2006.01)
*A61B 5/04* (2006.01)

(52) U.S. Cl. .......................... 607/118; 600/393; 607/46

(58) Field of Classification Search ................. 607/46, 607/118; 600/393
See application file for complete search history.

(56) References Cited

U.S. PATENT DOCUMENTS

| | | | | |
|---|---|---|---|---|
| 5,038,781 A | * | 8/1991 | Lynch | 607/61 |
| 5,199,428 A | * | 4/1993 | Obel et al. | 607/44 |
| 5,335,657 A | * | 8/1994 | Terry et al. | 607/45 |
| 5,344,438 A | * | 9/1994 | Testerman et al. | 607/118 |
| 5,545,219 A | | 8/1996 | Kuzma | |
| 5,578,061 A | * | 11/1996 | Stroetmann et al. | 607/4 |
| 5,711,316 A | | 1/1998 | Elsberry et al. | |
| 5,713,922 A | | 2/1998 | King | |
| 5,824,027 A | * | 10/1998 | Hoffer et al. | 607/118 |

(Continued)

OTHER PUBLICATIONS

International Search Report of PCT/US03/03003.

*Primary Examiner*—George Manuel
*Assistant Examiner*—Christopher A Flory
(74) *Attorney, Agent, or Firm*—Kenyon & Kenyon LLP

(57) ABSTRACT

The present invention provides a device and assembly for electrically and/or chemically stimulating individual ganglion and a plurality of ganglia of the nervous system, and particularly to ganglia of the sympathetic nerve chain. A device is provided that generally wraps around an individual ganglion and conforms to the shape of the ganglion without exerting excessive pressure on the ganglion to damage the ganglion. An assembly is also provided that includes an axially elongated shaft that can be positioned adjacent to the sympathetic nerve chain and that can receive a plurality of ganglion stimulators that can slidably engage with the outer surface of the shaft. As additional ganglia are desired to be stimulated, each of the plurality of ganglion stimulators can be added to the shaft to engage the outer surface of the shaft and can be positioned adjacent to the ganglia desired to be stimulated.

22 Claims, 10 Drawing Sheets

U.S. PATENT DOCUMENTS

| | | | |
|---|---|---|---|
| 6,104,957 A * | 8/2000 | Alo et al. | 607/46 |
| 6,178,349 B1 | 1/2001 | Kieval | |
| 6,458,157 B1 * | 10/2002 | Suaning | 623/6.63 |
| 6,511,500 B1 * | 1/2003 | Rahme | 607/1 |
| 7,340,298 B1 * | 3/2008 | Barbut | 607/2 |
| 2002/0116030 A1 | 8/2002 | Rezai | |
| 2003/0060857 A1 * | 3/2003 | Perrson et al. | 607/44 |
| 2003/0236558 A1 * | 12/2003 | Whitehurst et al. | 607/45 |
| 2005/0075701 A1 * | 4/2005 | Shafer | 607/72 |
| 2005/0234523 A1 * | 10/2005 | Levin et al. | 607/42 |

* cited by examiner

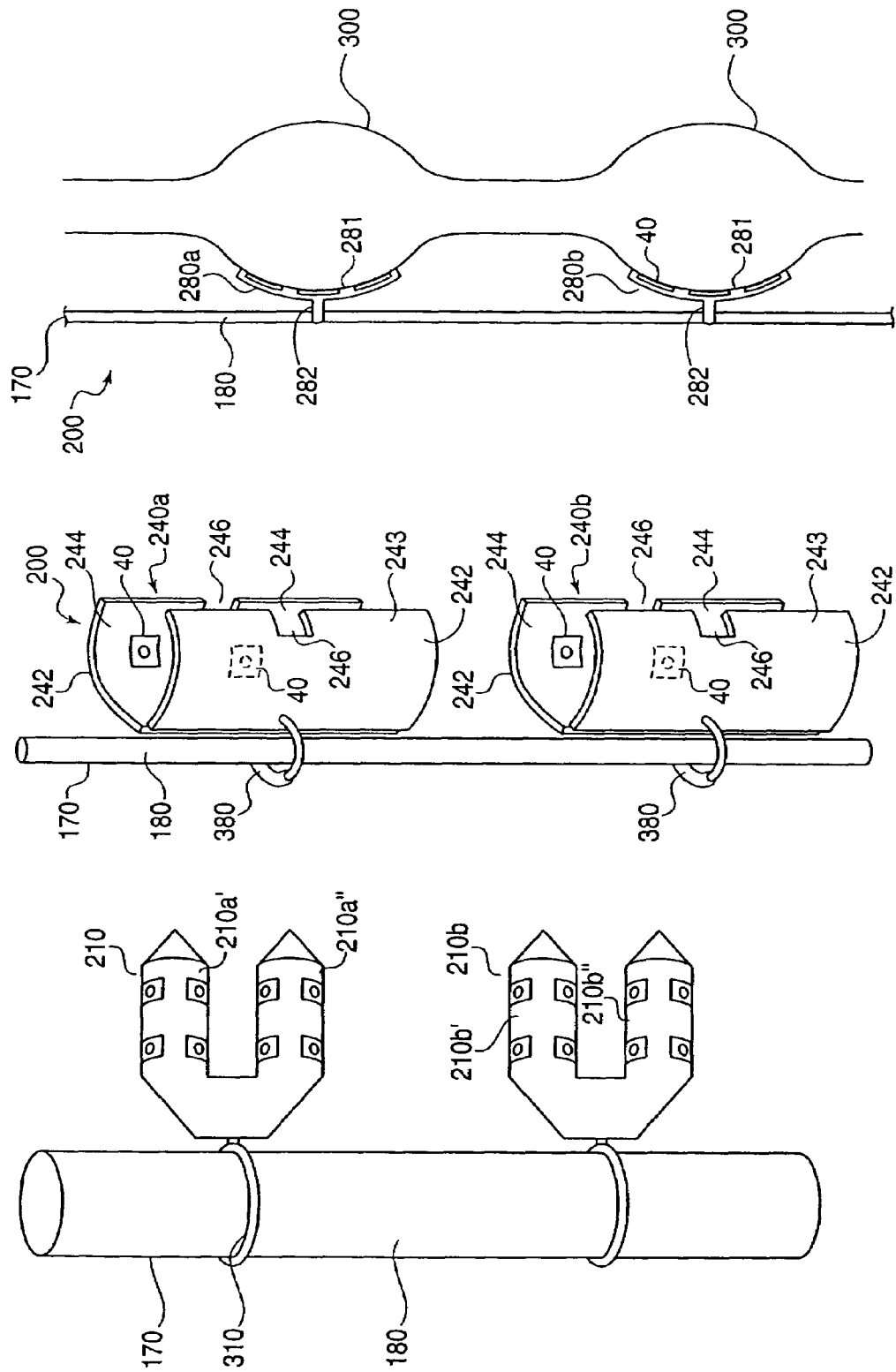

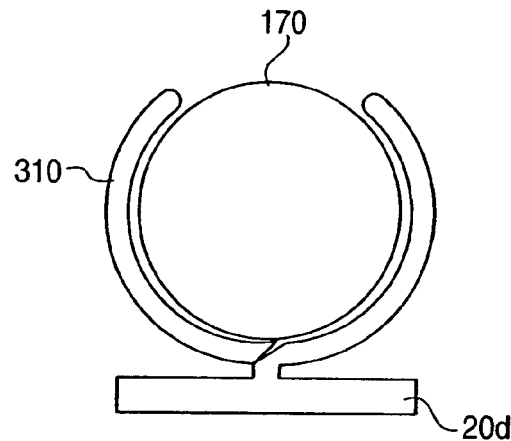 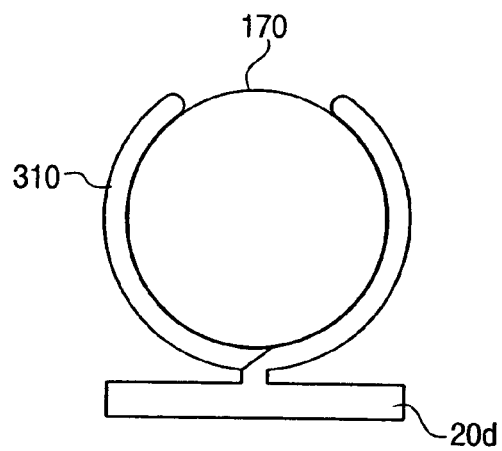
FIG. 18A   FIG. 18B
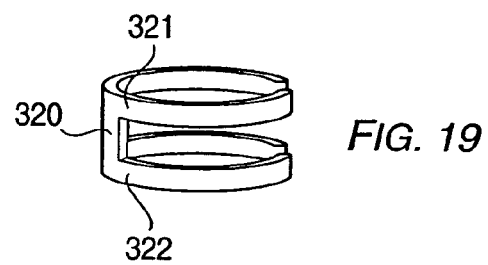
FIG. 19
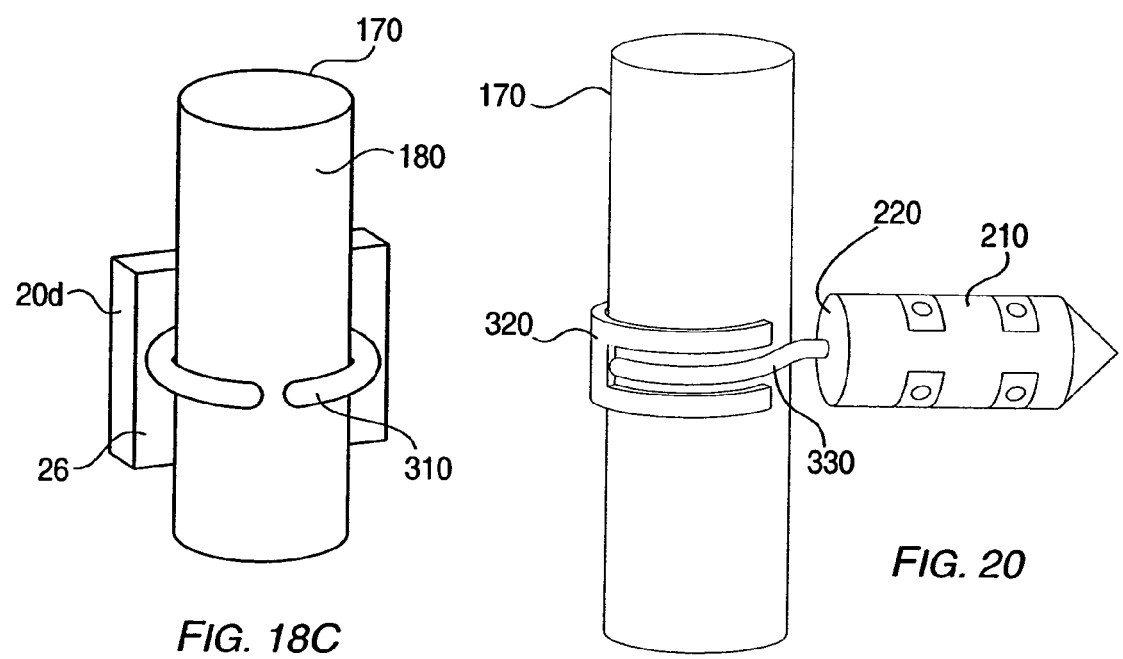
FIG. 18C   FIG. 20

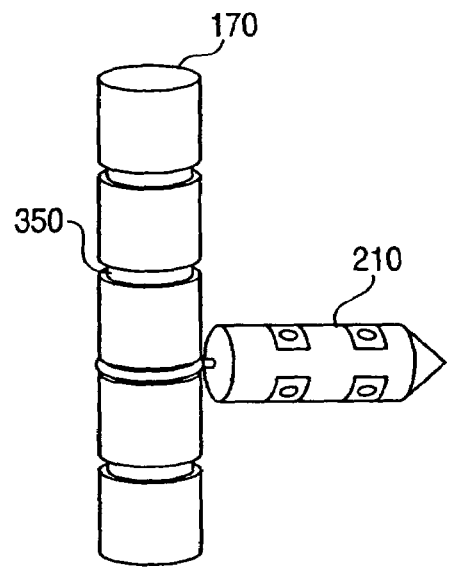
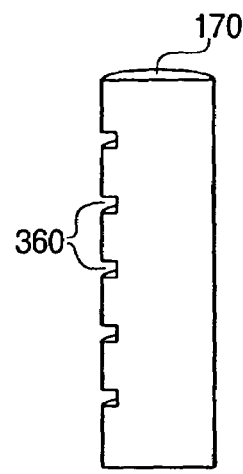
FIG. 21
FIG. 22
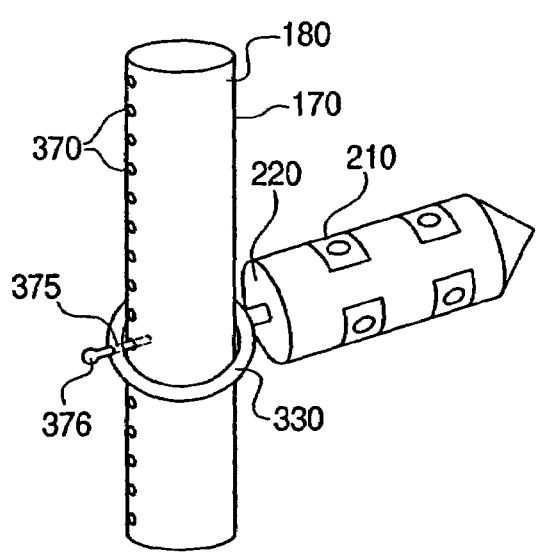
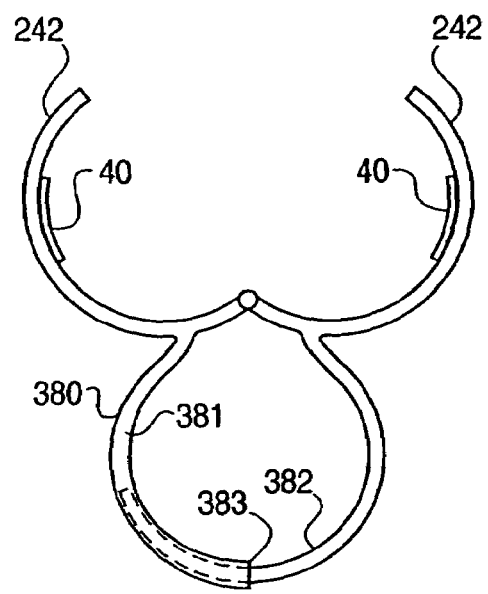
FIG. 23
FIG. 24

US 7,477,945 B2

DELIVERY DEVICE FOR STIMULATING THE SYMPATHETIC NERVE CHAIN

CROSS-REFERENCE TO RELATED U.S. APPLICATION

This is a 371 application of PCT/US03/03003 filed 03 Feb. 2003, the content of which is incorporated herein by reference.

This application also claims priority to Provisional U.S. Application No. 60/353,700 filed Feb. 1, 2002, which is incorporated herein by reference.

FIELD OF THE INVENTION

The present invention relates to a device, assembly, and method of chemically and/or electrically stimulating neural tissue to affect a physiological condition.

BACKGROUND OF THE INVENTION

Electrical stimulation of the brain and spinal cord has been used to affect a select number of physiological conditions such as Parkinson's disease, essential tremors, dystonia, chronic pain, and certain psychiatric disorders. Such therapy is often utilized in a subset of the respective patient population that is unresponsive to other forms of therapy, including traditional pharmacotherapy. There are, however, several other autonomic-related diseases such as cardiac, respiratory, renal diseases, and other diseases associated with autonomic function for which a subset of the patient population is also unresponsive to other forms of treatment.

Stimulation of a sympathetic nerve chain, which extends longitudinally along a side of the vertebral column and which includes a chain of sympathetic ganglia, may be used to alleviate the symptoms of these autonomic-related diseases, even though these diseases are not necessarily related to a dysfunction in the sympathetic ganglia. Because sympathetic ganglia have afferent pathways from the central nervous system and efferent pathways to visceral end organs, modulation of sympathetic ganglia may affect both the end organs and the central nervous system. Methods of electrically and/or chemically stimulating the sympathetic ganglia or the sympathetic nerve chain are described in more detail in the inventor's co-pending application 2002/0116030, which is incorporated by reference herein.

Current electrode devices, such as nerve cuff electrodes, however, are not designed in a manner to efficiently effect stimulation to sympathetic ganglia. Therefore, there is an unmet need for a delivery device that effectively provides stimulation to the sympathetic nerve chain to modulate individual sympathetic ganglion as well as multiple sympathetic ganglia.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 15 is a side view of an alternative embodiment of an assembly according to the present invention.

FIG. 16 is a side perspective view of an alternative embodiment of an assembly according to the present invention.

FIG. 17 is a side view of an alternative embodiment of an assembly according to the present invention.

FIG. 18A-B is a top plan view of an embodiment of an engagement mechanism according to the present invention.

FIG. 18C is a perspective view of an alternative embodiment of an engagement mechanism according to the present invention.

FIG. 19 is a side perspective view of an alternative embodiment of an engagement mechanism according to the present invention.

FIG. 20 is a side perspective view of the engagement mechanism of FIG. 19 according to the present invention in a deployed position.

FIG. 21 is a side perspective view of an alternative embodiment of an engagement mechanism according to the present invention.

FIG. 22 is a side view of an alternative embodiment of an engagement mechanism according to the present invention.

FIG. 23 is a side perspective view of an alternative embodiment of an engagement mechanism according to the present invention.

FIG. 24 is a top plan view of an alternative embodiment of an engagement mechanism according to the present invention.

SUMMARY OF THE INVENTION

Figure 1:
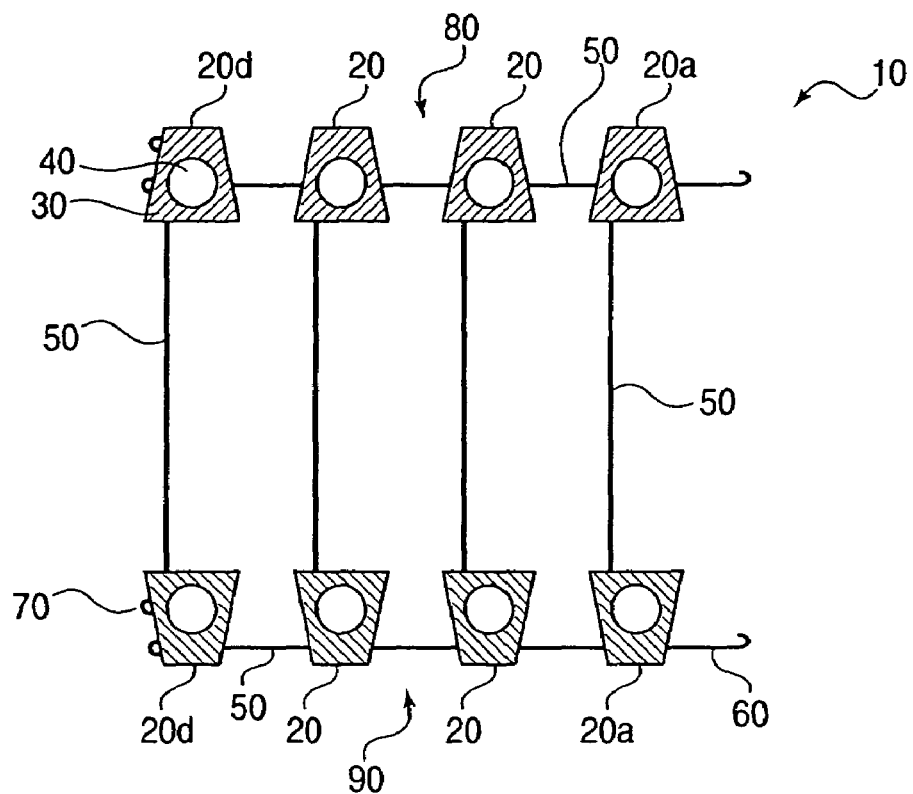
FIG. 1 is an inner view of an embodiment of a device according to the present invention.

The present invention relates to a device, assembly, and method for modulating a a ganglion or ganglia of the nervous system. In a preferred embodiment, the present invention relates to modulating a ganglion or ganglia of the sympathetic nerve chain by chemically and/or electrically stimulating the ganglion or ganglia. One embodiment of the present invention provides a delivery device to stimulate a ganglion including a first series of flexibly connected delivery contacts. A leading one of the first series of flexibly connected delivery contacts is engagably associated with a trailing one of the first series of flexibly connected delivery contacts in an operative position of the delivery device. The delivery device also includes a second series of flexibly connected delivery contacts flexibly connected to the first series of flexibly connected delivery contacts. A leading one of the second series of flexibly connected delivery contacts is engagably associated with a trailing one of the second series of flexibly connected delivery contacts in an operative position of the delivery device. In this embodiment of the present invention, the delivery device maintains a substantially ovoid configuration when in an operative position.

The present invention also provides an assembly for stimulating ganglia and preferably sympathetic ganglia of the sympathetic nerve chain including an axially elongated shaft having an inner surface and an outer surface. The assembly also includes a first probe having a distal end and a proximal end, the distal end of the first probe slidably engagable with the outer surface of the shaft and the proximal end of the first probe insertable in a ganglion. The first probe also includes at least one delivery element disposed thereon. The assembly further includes a second probe having a distal end and a proximal end, the distal end of the second probe slidably engagable with the outer surface of the shaft and the proximal end of the second probe insertable in a ganglion. The second probe also includes at least one delivery element disposed thereon. When the assembly is in an operative position, the distal end of the first probe and the distal end of the second probe are securely attached to the outer surface of the shaft.

The present invention further provides an assembly for stimulating ganglia, and preferably sympathetic ganglia of the sympathetic nerve chain including an axially elongated shaft having an inner surface and an outer surface. The assembly further includes a first terminal member having a distal end and a proximal end, the distal end of the first terminal member slidably engagable with the outer surface of the shaft and the proximal end of the first terminal member having a generally concave configuration and adjacently positionable to a ganglion. The first terminal member also includes at least one delivery element disposed thereon. The assembly further includes a second terminal member having a distal end and a proximal end, the distal end of the second terminal member slidably engagable with the outer surface of the shaft and the proximal end of the second terminal member having a generally concave configuration and adjacently positionable to a ganglion. The second terminal member also includes at least one delivery element disposed thereon. In an operative position of the assembly, the distal end of the first terminal member and the distal end of the second terminal member are securely attached to the outer surface of the shaft.

The present invention moreover provides an assembly for stimulating ganglia and preferably sympathetic ganglia of the sympathetic nerve chain including an axially elongated shaft having an inner surface and an outer surface. The assembly further includes a first delivery structure slidably engagable with the outer surface of the shaft, the first delivery device comprising a first pair of connected clamping members. Each of the first pair of connected clamping members has an outer wall and an inner concave wall and each of the inner concave walls of each of the first pair of connected clamping members has at least one delivery element disposed thereon. The assembly further includes a second delivery structure slidably engagable with the outer surface of the shaft, the second delivery device comprising a second pair of connected clamping members. Each of the second pair of connected clamping members has an outer wall and an inner concave wall and each of the inner concave walls of each of the second pair of connected clamping members has at least one delivery element disposed thereon. When the assembly is in an operative position, the first and second delivery structures are securely attached to the outer surface of the shaft.

The present invention also provides a method of stimulating a ganglia including encasing a delivery device around at least a portion of a ganglion, wherein the stimulation delivery device comprises at least one delivery element and providing a stimulation signal to the at least one delivery element to stimulate the ganglion.

The present invention further provides a method of stimulating sympathetic ganglia including positioning an axially elongated shaft adjacent to the sympathetic nerve chain, the shaft having an outer surface. The method further includes slidably engaging a first ganglion stimulator with the outer surface of the shaft, the first ganglion stimulator comprising at least one first delivery element. The method moreover includes placing the first ganglion stimulator adjacent to a first ganglion, securing the first ganglion stimulator to the outer surface of the shaft, and providing a stimulation signal to the at least one first delivery element to stimulate the first ganglion.

DETAILED DESCRIPTION OF THE INVENTION

The present invention relates to a device, assembly, and method of modulating a ganglia of the nervous system. Non-limiting examples of such ganglia include cranial and extra-cranial ganglia including spenopalatine ganglion, otic ganglion, pterygopalatine ganglion, and ciliary ganglion. In a preferred embodiment, the present invention relates to modulating ganglion or ganglia of the sympathetic nerve chain by chemically and/or electrically stimulating the ganglion or ganglia. Referring to FIG. 1, one embodiment of the present invention provides a series of delivery contacts 20 that are flexibly connected to each other and that are designed to wrap around an individual ganglion to provide stimulation thereto. A delivery contact 20 generally includes a delivery element 40 (which may be an electrode in the case of electrical stimulation or a drug port in the case of chemical stimulation) disposed atop or co-planar with a pad 30. In particular, this embodiment provides a delivery device 10 that includes a first series 80 of delivery contacts 20 and a second series 90 of delivery contacts 20. Each delivery contact 20 of first series 80 is connected to an adjacent delivery contact 20 of the first series 80 by flexible connectors 50 and each delivery contact 20 of the second series 90 is connected to an adjacent delivery contact 20 of the second series 90 by flexible connectors 50. Furthermore, each delivery contact 20 of the first series 80 is connected to an adjacent delivery contact 20 of the second series 90 by flexible connectors 50. Within each series 80 and 90, a leading one 20a of the delivery contacts 20 of series 80 and 90 is engagably associable with a respective trailing one 20d of the delivery contacts 20 of series 80 and 90. In other words, a leading one 20a of the first series 80 of delivery contacts 20 is engagably associable with a trailing one 20d of the first series 80 of delivery contacts 20. Similarly, a leading one 20a of the second series 90 of delivery contacts 20 is engagably associable with a trailing one 20d of the second series 90 of delivery contacts 20.

Figure 2:
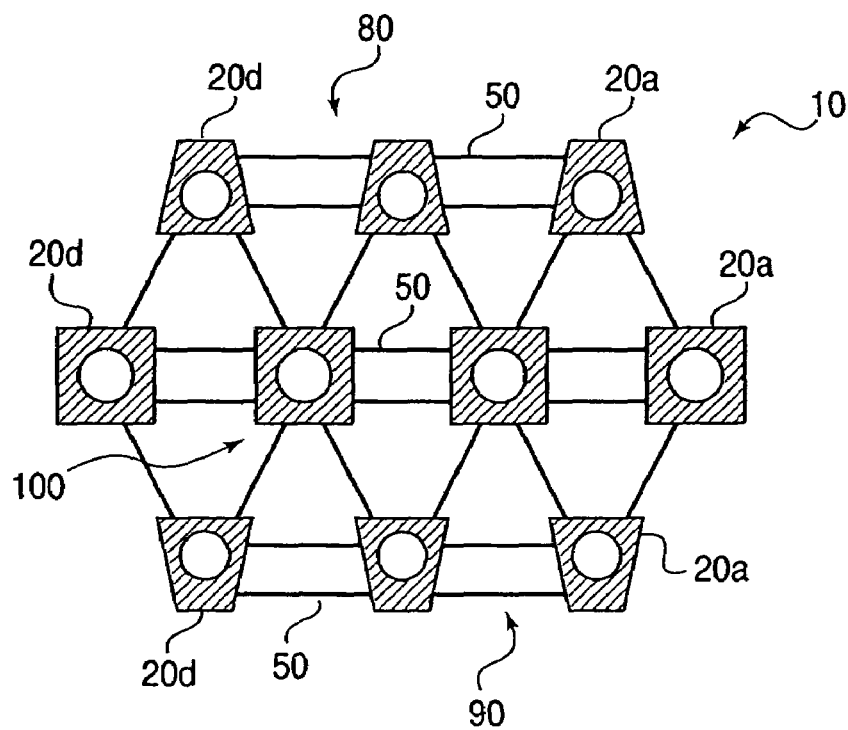
FIG. 2 is an inner view of an alternative embodiment of a device according to the present invention.

Referring to FIG. 2, in a preferred embodiment, delivery device 10 includes a first series 80 of delivery contacts 20 and a second series 90 of delivery contacts 20 as described above and additionally includes a third series 100 of delivery contacts 20 located between and connected to first series 80 and second series 90. In particular, each delivery contact 20 of third series 100 is connected to an adjacent delivery contact 20 of third series 100 by flexible connectors 50. Furthermore, each delivery contact 20 of third series 100 is connected to an adjacent delivery contact 20 of second series 90 by flexible connectors 50 and to an adjacent delivery contact 20 of first series 80 by flexible connectors 50. A leading one 20a of the third series 100 of delivery contacts 20 is engagably associable with a trailing one 20d of third series 100 of delivery contacts 20. As will be appreciated by one skilled in the art, delivery device 10 can include any number of series of delivery contacts 20 to wrap around a ganglion and provide stimulation thereto.

Figure 3:
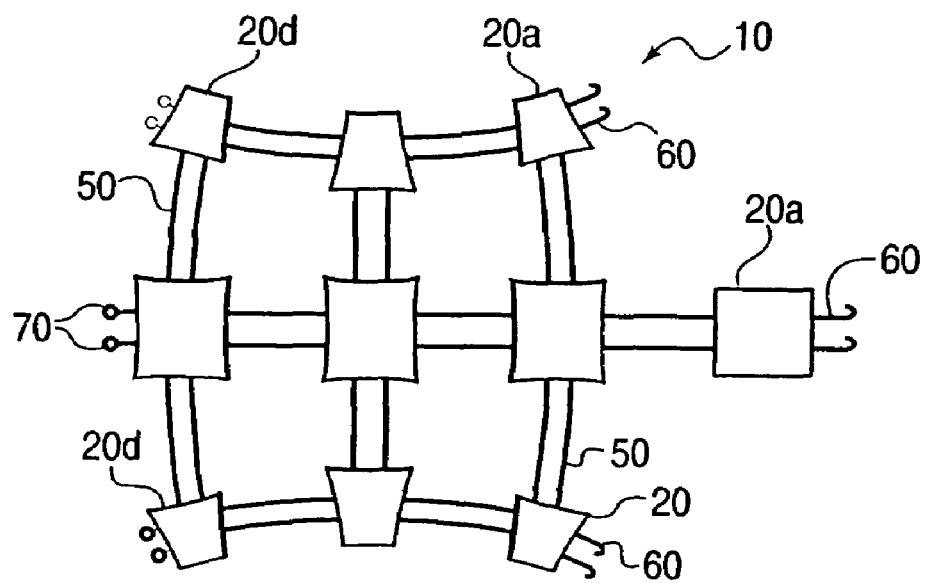
FIG. 3 is an outer view of an alternative embodiment of a device according to the present invention.

Referring to FIG. 3, notwithstanding whether delivery device 10 includes a first and second series 80 and 90 of delivery contacts 20 or a first, second, and third series 80, 90, and 100 of delivery contacts 20, preferably first series 80 is arranged in a concave configuration and second series 90 is arranged in a convex configuration.

Figure 4:
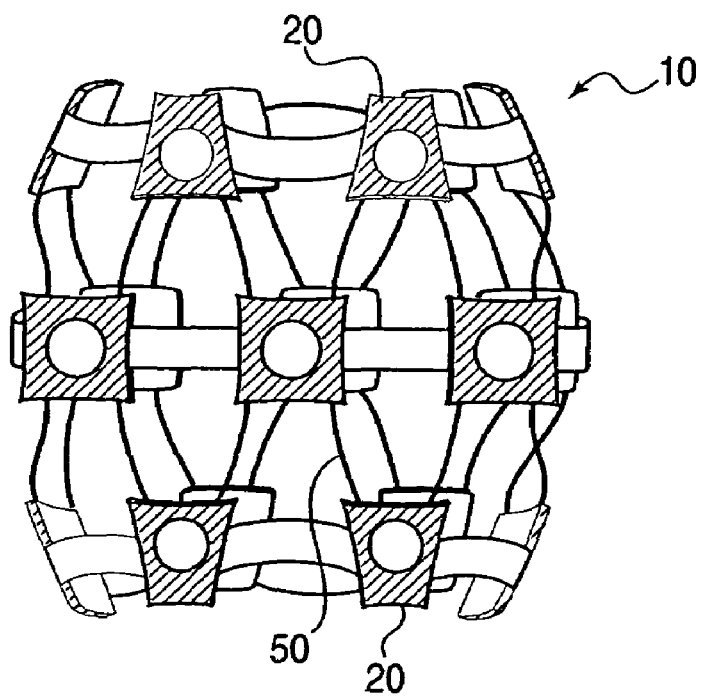
FIG. 4 is a perspective view of the device of FIG. 3 according to the present invention in an operative position.

Referring to FIG. 4, when in a operative position, delivery contacts 20a and delivery contacts 20d of first series 80, second series 90, and third series 100 are engagably associated with each other so that delivery device 10 forms a substantially ovoid configuration to conform to the configuration of a ganglion. In the context of this embodiment of the present invention, by "substantially ovoid configuration" is generally meant all plane sections of delivery device 10 are ellipses or circles in an operative position of device 10. In the context of this embodiment of the present invention, by "engagably associated" is generally meant that leading delivery contact 20a and trailing delivery contact 20d are associated with each other, although not necessarily contacting each other, such that the respective series to which they belong form a secure elliptical or circular configuration in an operative position of device 10.

Figure 5:
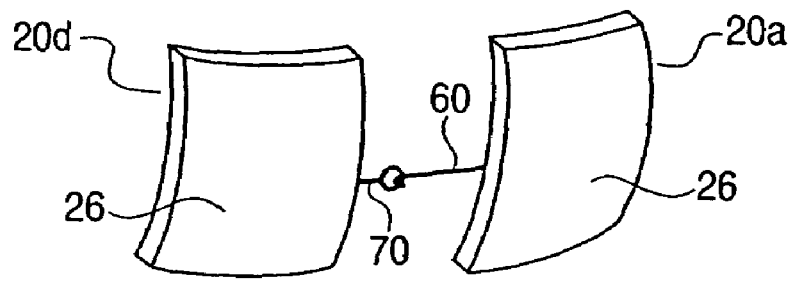
FIG. 5 is an outer perspective view of a component of a device according to the present invention.
Figure 6:
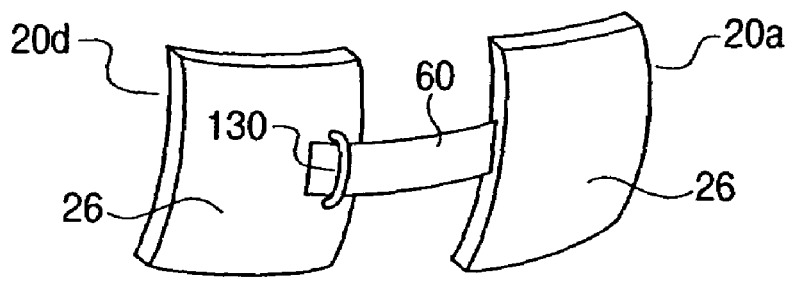
FIG. 6 is an outer perspective view of an alternative embodiment of a component of a device according to the present invention.
Figure 7:
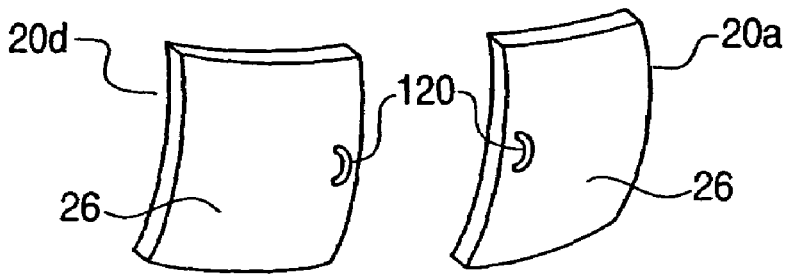
FIG. 7 is an outer perspective view of an alternative embodiment of a component of a device according to the present invention.

Delivery contacts 20a and 20d may engagably associate with each other by any means known in the art, such as by any fastening mechanisms including a hook-and eye mechanism, a hook and loop mechanism such as that employed under the tradename VELCRO, buckles, straps, snaps, clamps, staples, and any type of male-female mating members such as nuts and screws, rivets, and the like. For example, as illustrated in FIGS. 1, 3, and 5, a free end 60 of flexible connector 50 immediately adjacent to delivery contact 20a in a direction opposite trailing delivery contact 20d may have a hook-shape and delivery contact 20d may define or have attached thereto a loop-shaped structure 70 to engagingly receive free end 60. Alternatively, as seen is FIG. 6, delivery contact 20d may define or have attached thereon buckle 130 through which to receive free end 60 of flexible connector 50. Alternatively, as seen in FIG. 7, delivery contacts 20a and 20d may define or have attached thereon suturing rings 120 through which surgical threading can pass to engagably associate 20a and 20d in an operative position of delivery device 10.

Figure 8:
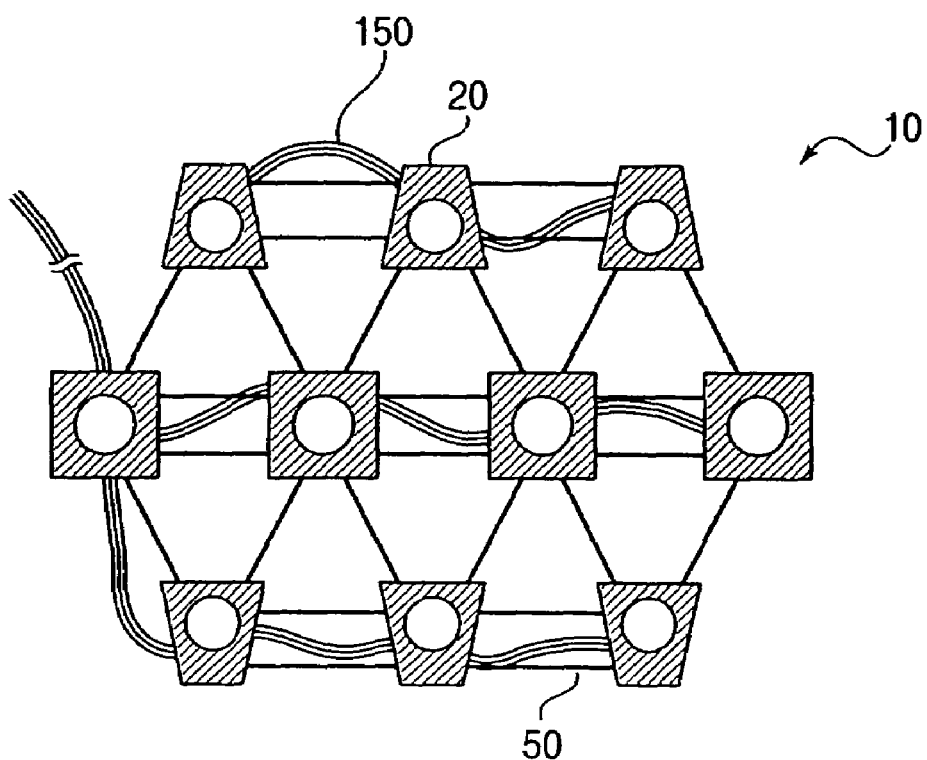
FIG. 8 is an inner view of a device according to the present invention.

Referring to FIG. 8, in order to deliver a stimulation signal to each delivery contact 20, a conduit 150 communicates with each delivery contact 20. In particular, the distal end of conduit 150 communicates with each delivery contact 20 and the proximal end of conduit 150 is coupled to a stimulation signal controller. In the case of electrical stimulation, each delivery contact 20 includes at least one delivery element 40 that is an electrode, conduit 150 is a conduction cable, and the stimulation signal controller is a signal pulse generator, radio frequency system, or any other generator of electrical energy. In the case of chemical stimulation, each delivery contact 20 includes at least one delivery element 40 that is a drug port, conduit 150 is a catheter, and the stimulation signal controller is a drug pump, or any other structure than can deliver chemical agents to delivery element 40. In the case of delivering electrical and chemical stimulation, the stimulation signal controller may be both a drug pump and pulse generator.

Figure 9:
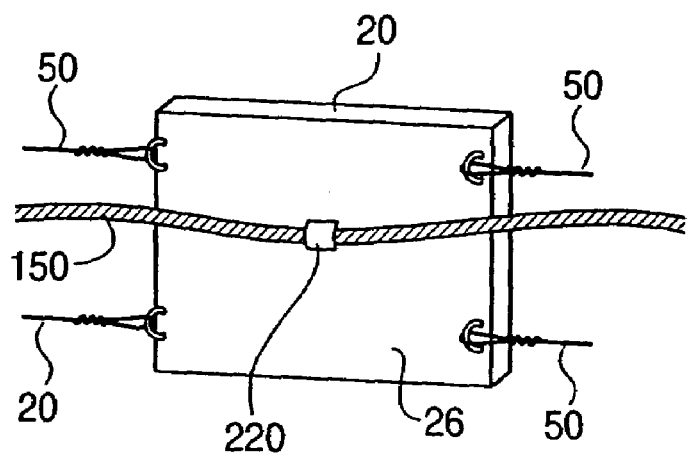
FIG. 9 is an outer perspective view of a component of a device according to the present invention.

Referring to FIG. 9, each delivery contact 20 may include a fastening port 220 to securely receive cable 150.

With respect to details of individual components of delivery device 10, the particular specifications of delivery device 10 depend on the characteristics of the ganglion being stimulated, which is related to characteristics of the patient, such as age, height, or gender, as well as the type of ganglion desired to be stimulated. With this in mind, each series of delivery contacts 20 may include any number of delivery contacts 20, separated by any distance and of any size and configuration, to conform to the configuration of a ganglion in an operative position of device 10. In a preferred embodiment of device 10, including a first series 80, second series 90, and third series 100, first series 80 includes four delivery contacts 20, second series 90 includes four delivery contacts 20, and third series 100 includes four delivery contacts. Preferably, in a non-operative position, the distance separating adjacent delivery contacts 20 within a series is between about one millimeters and about three millimeter and the distance separating adjacent delivery contacts 20 between series is between about one millimeters to about six millimeters. Preferably, in an operative position, each series of electrical contacts 20 has a diameter between about two millimeter and about ten millimeters with the diameter of the third series 100 being greater than the diameter of the first series 80 and the second series 90. Although FIG. 1 illustrates each delivery contact 20 being connected to only one other delivery contact 20 in another series, delivery contacts 20 may be also be connected to more than one other delivery contact 20 in another series. For example, as illustrated in FIG. 2, each delivery contact 20 in first series 80 is connected to two other delivery contacts 20 in second series 90.

Figure 10:
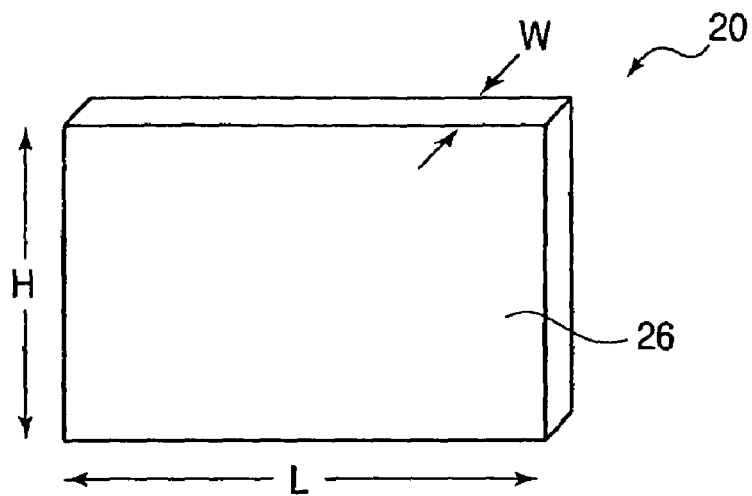
FIG. 10 is an outer perspective view of a component of a device according to the present invention.
Figure 11:
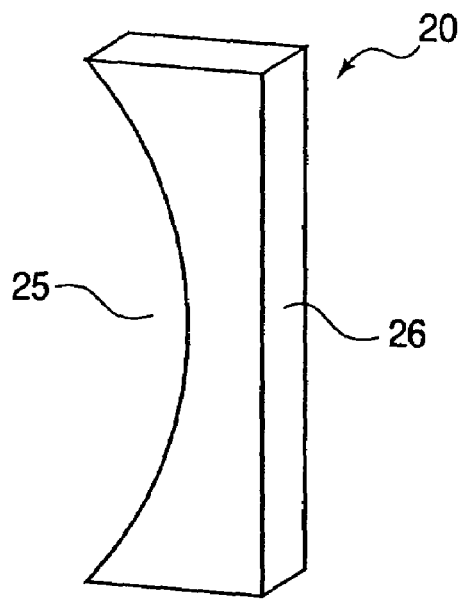
FIG. 11 is a side perspective view of an alternative embodiment of a component of a device according to the present invention.

Each delivery contact 20 may have any size or configuration suitable for stimulating a ganglion. Referring to FIG. 10, in a preferred embodiment delivery contact 20 has a length L between about one millimeter and about three millimeters, a height H of between about one millimeter and about three millimeter, and a width W of between about 0.1 and about 0.2 millimeters. Referring to FIG. 11, each delivery contact 20 has an inner surface 25, which faces a ganglion in an operative position of the device and an outer surface 26. In a preferred embodiment, inner surface 25 of each delivery contact 20 has a concave configuration to conform to the shape of a ganglion. Also in a preferred embodiment, delivery contacts 20 of first series 80 and second series 90 have a trapezoidal configuration, as illustrated in FIG. 1-4.

Figure 12:
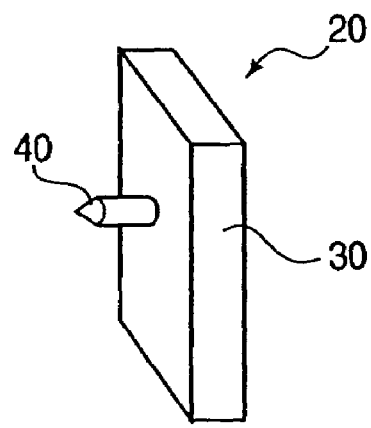
FIG. 12 is a side view of an alternative embodiment of a component of a device according to the present invention.

Each delivery contact 20 of each series 80, 90, and optionally 100 may comprise a single delivery element 40 of any shape or size; a single delivery element of any shape or size that is co-planar with or disposed atop a pad 30; or more than one delivery element 40 of any shape or size that is co-planar with or disposed atop pad 30. Delivery elements 40 may be mounted in or on pads 30 through any well known manufacturing method such as through the use of medical adhesives or forming the delivery elements 40 in pads 30 at the time pads 30 are molded. Referring to FIG. 12, in a preferred embodiment, delivery element 40 is a pin-shaped structure that can be inserted in a ganglion.

Pads 30 may be of any shape or size and are fabricated of any biocompatible material. For example, pad 30 may be fabricated of any plastic or semi-rigid material including silicone rubber, polyurethane, or other thermoplastics and polymers such as nylon, polytetrafluoroethylene (PTFE) or the like. In a preferred embodiment, pad 30 is fabricated of an insulation material.

Although delivery elements 40 generally serve to deliver stimulation to a ganglion, delivery elements 40 may also detect chemical or electrical activity of a ganglion. For example, first series 80 and second series 90 of delivery contacts 20 may delivery stimulation to a ganglion while third series 90 of delivery contacts 20 act as sensors and detect activity of a ganglion in response to or in preparation of stimulation. Alternatively, alternate ones of first, second, and third series 80, 90, and 100 may serve stimulating or sensing functions. Other means of combining stimulation and sensing functions will be readily known to one of skill in the art and such means are within the scope of the present invention.

With respect to connectors 50, connectors 50 may be manufactured of any elastic, biocompatible, and preferably non-absorbent material such as, for example, polyisoprene, natural rubber, polybutadiene, silicone, a blend of such materials, or the like. Connectors 50 may be attached to delivery contacts 20 by any fastening mechanism such as adhesive bonding, a hook-and eye mechanism, a hook and loop mechanism such as that employed under the tradename VELCRO, buckles, straps, snaps, clamps, staples, and any type of male-female mating members such as nuts and screws, rivets, and the like. In a preferred embodiment, connectors 50 are attached to delivery contacts 20 by a releasable fastening mechanism such that connectors 50 between series can be disconnected and then subsequently re-connected.

The present invention also provides an assembly for stimulating ganglia of the sympathetic nerve chain. In general, this assembly includes an axially elongated shaft that is placed adjacent to a sympathetic nerve chain. The assembly further includes a plurality of ganglion stimulators that can be coupled to the shaft in a position adjacent to a desired ganglion of the sympathetic nerve chain desired to be stimulated. As additional ganglia are desired to be stimulated, additional ganglion stimulators can be coupled to the shaft. Because the exact location of the sympathetic ganglia desired to be stimulated may vary from patient to patient, such an assembly allows the shaft to be placed adjacent to any sympathetic nerve chain and to slidably position the ganglion stimulators along the longitudinal axis of the shaft, until the ganglion stimulators are adjacent to the desired ganglia. By "ganglion stimulators" is generally meant any device comprising at least one delivery element 40, which can be either an electrode or drug port, that can provide stimulation to a sympathetic ganglion. Although preferred embodiments of ganglion stimulators are described herein, the present invention contemplates other ganglion stimulators which can achieve the same effect as the preferred embodiments according to the present invention.

Figure 13:
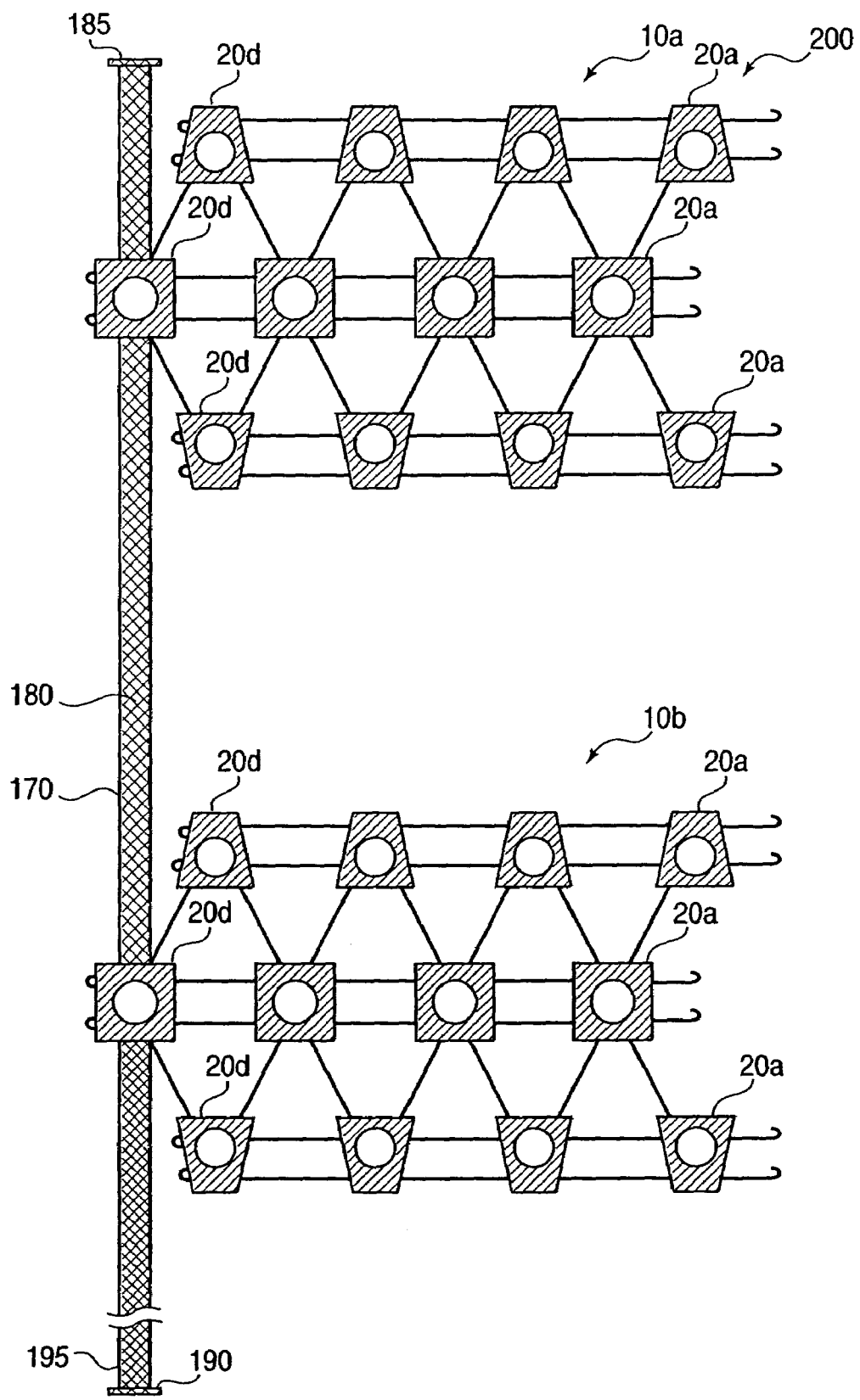
FIG. 13 is an inner view of an embodiment of an assembly according to the present invention.

In particular, referring to FIG. 13, one embodiment of an assembly 200 according to the present invention includes a ganglion stimulator that is a delivery device 10 as described in detail above. Assembly 200 further includes an axially elongated shaft 170 having a proximal end 185, a distal end 195, an inner surface (not shown) and an outer surface 180 that is slidably engagable with delivery device 10. Preferably a limit stop 190 is detachably coupled to outer surface 180 of shaft 170 and preferably a lumen extends through shaft 170 to house a conduit to delivery electrical or chemical stimulation to delivery contacts 20 of delivery device 10 (or to delivery elements 40 of any other ganglion stimulator). Shaft 170 may be rigid, semi-rigid, or flexible. Although this embodiment may be used with only one delivery device 10, in a preferred mode of utilizing assembly 200, a plurality of delivery devices 10 are employed such that each delivery device 10 is associated with a separate ganglion in the sympathetic nerve chain. The number of delivery devices 10 employed is a function of the number of ganglion desired to be stimulated. In a preferred use, in a loading position of assembly 200, trailing electrical contact 20d of series 80, series 90, and/or series 100 (in embodiments where series 100 is present) of a first stimulation device 10a is engaged with outer surface 180 of shaft 170 such that the first delivery device 10a is capable of slidably engaging outer surface 180 and axially sliding along shaft 170. Alternatively, another delivery contact 20 (or any other anchoring structure) adjacent to trailing delivery contact 20d in a direction opposite leading delivery contact 20a may be coupled to outer surface 180. Limit stop 190 prevents first delivery device 10a from slidably exiting shaft 170 from either proximal end 185 or distal end 195 in a loading position of assembly 200. After reaching the desired ganglion to be stimulated, assembly 200 assumes an operative position, and first delivery device 10a is securely attached to shaft 170 (by securely attached trailing delivery contact 20d to outer surface 180) and leading delivery contacts 20a of series 80, 90, and 100 are engagedly associated with respective trailing delivery contacts 20d of series 80, 90, and 100 to wrap around the desired ganglion. If another ganglion is desired to be stimulated, then the same procedure is followed with a second delivery device 10b. Preferably limit stop 190 is placed inferior or superior to trailing delivery contact 20d of first delivery device 10a that is coupled to shaft 180 such that the slidable entry of second delivery device 10b does not interfere with the position of first delivery device 10a.

Figure 14:
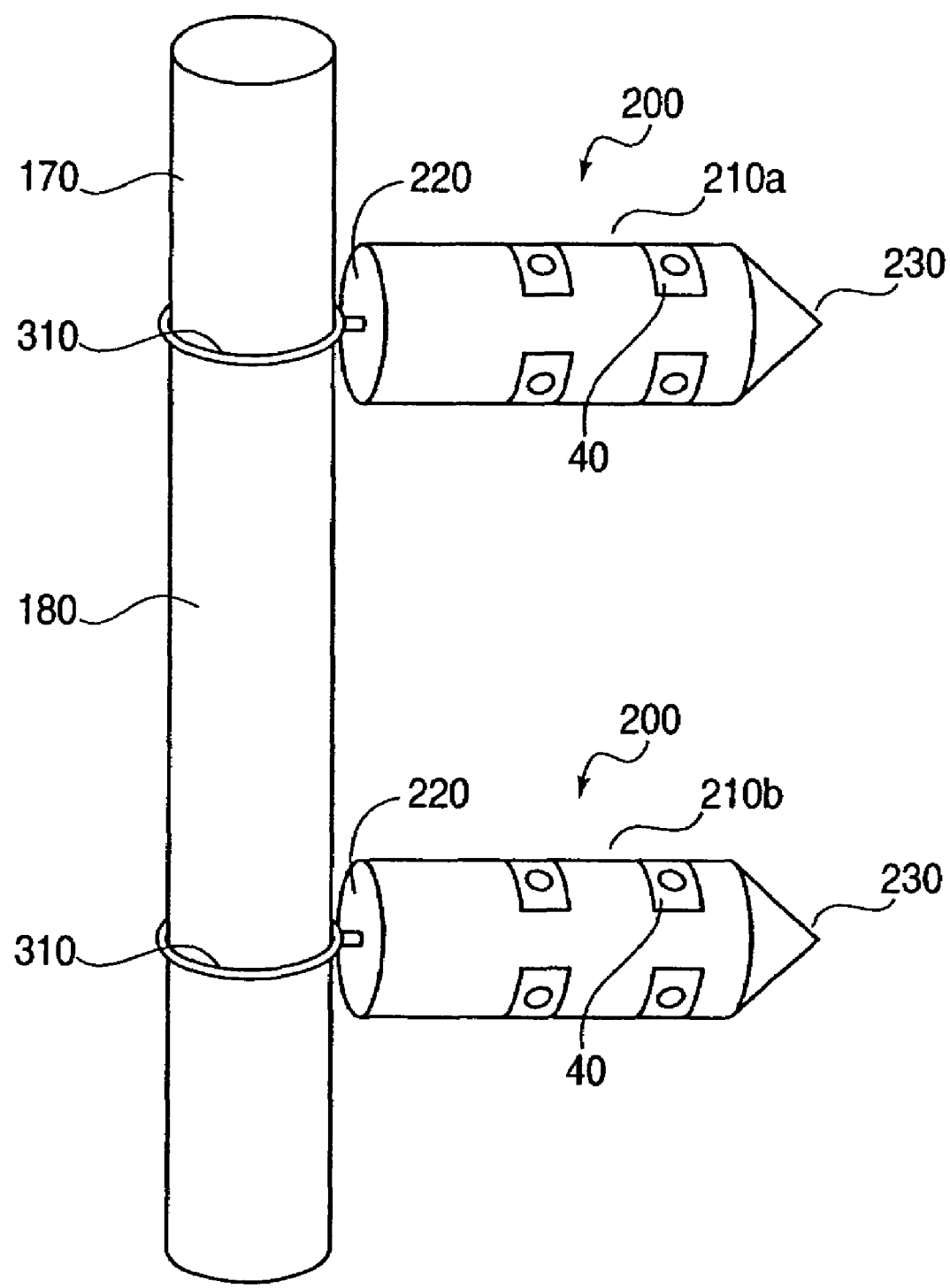
FIG. 14 is a side perspective view of an alternative embodiment of an assembly according to the present invention.

Referring to FIG. 14, in an alternative embodiment, assembly 200 includes an axially elongated shaft 180 as described above and a ganglion stimulator that is a first probe 210a having at least one delivery element 40 disposed thereon and having a distal end 220 and a proximal end 230. In a loading position of assembly 200, distal end 220 of first probe 210a is slidably engagable with outer surface 180 of shaft 170 and proximal end 230 of first probe 210a is insertable in a sympathetic ganglion. Assembly 200 further includes another ganglion stimulator that is a second probe 210b including at least one delivery element 40 thereon and having a distal end 220 and a proximal end 230. In a loading position of assembly 200, distal end 220 of second probe 210b is also slidably engagable with outer surface 180 of shaft 170 and proximal end 230 is insertable into a ganglion. In an operative position of assembly 200, distal ends 220 of first probe 210a and second probe 210b are secured attached to outer surface 180 of shaft 170 and proximal ends 230 of first probe 210a and second probe 210b are inserted into respective ganglia. Probes 210 may define either a single prong, as illustrated in FIG. 14, or may define dual prongs, 210' and 210," as illustrated in FIG. 15.

Referring to FIG. 16, in an alternative embodiment, assembly 200 includes shaft 170 as described above and ganglion stimulators that are delivery structures 240, each delivery structure 240 slidably engagable with outer surface 180 of shaft 170 in a loading position of assembly 200. In particular, assembly 200 includes a first delivery structure 240a and a second delivery structure 240b, each delivery structure 240 including a pair of pivotably connected clamping members 242 that are designed to encase all or a portion of a sympathetic ganglion. Each clamping member 242 has an outer wall 243 and an inner concave wall 244, which faces a ganglion. Each of the inner concave walls 244 have at least one delivery element 40 disposed thereon. Because each delivery structure 240 is designed to encase all or a portion of a ganglion, each delivery structure 240 is capable of operably moving from an open position wherein each delivery structure 240 is placed around a respective ganglion and a closed or operative position wherein each delivery structure 240 encloses all or a portion of a respective ganglion. Delivery structures 240 may include any means known in the art to effectuate such operable movement, although in a preferred embodiment, clamping members 242 are hingedly connected to each other. Furthermore, although delivery structures 240 may have numerous configurations, such as spherical, conical, or cylindrical, in a preferred embodiment, delivery structures 240 have as ovoid configuration in a closed or operative position such that they conform to the configuration of a sympathetic ganglion. In a further preferred embodiment, each inner wall 244 and outer wall 243 of each clamping member 242 defines a notch 246 such that in a closed or operative position of each delivery structure 240, the post-ganglionic fibers extending from each ganglion are positioned within the aperture created by the mutually confronting notches 246 of each delivery structure 240. In a loading position of assembly 200, first delivery structure 240a and second delivery structure 240b are each slidably engaged with outer surface 180 of shaft 170 and each placed in a open position next to the desired ganglia to be stimulated. Assembly 200 then assumes an operative position and clamping members 242 of each delivery structures 240 are arranged in a closed position such that respective clamping members 242 mutually confront each other and each delivery structure 240 is securely attached to outer surface 180 of shaft 170.

Referring to FIG. 17, in an alternative embodiment, assembly 200 includes a shaft 170 as described above and ganglion stimulators that are terminal members 280 that are slidably engagable with outer surface 180 of shaft 170 in a loading position of assembly 200. In particular, ganglion stimulators include a first terminal member 280a and a second terminal member 280b, each terminal member 280 having a proximal end 281, which has a generally concave configuration and includes at least one delivery element 40 disposed thereon, and a distal end 282. In a loading position of assembly 200, distal ends 282 are slidably engagable with outer surface 180 of shaft 170 and proximal ends 281 are adjacently positionable to respective ganglia 300. In an operative position of assembly 200, distal ends 282 of terminal members 280 are securely attached to outer surface 180 of shaft 170 and proximal ends 281 are positioned adjacent to the respective ganglia 300.

Although the above-mentioned embodiments of assembly 200 have been described in relation to sympathetic ganglia of the sympathetic nerve chain, it is understood that such embodiments may also be used in other ganglia in the body, particularly ganglia that are serially arranged.

Notwithstanding the particular embodiment of assembly 200, each ganglion stimulator is associated with an engagement mechanism that allows each ganglion stimulator to slidably engage outer surface 180 of shaft 170 during a loading position of the respective assembly 200 yet securely attach to outer surface 180 of shaft 170 during an operative position of respective assembly 200. Although exemplary engagement mechanisms will now be described in relation to only specific embodiments of assembly 200 for the sake of illustration, it is understood that such engagement mechanisms are generally interchangeable for all the above-described embodiments of assembly 200. Referring to FIG. 18, in one embodiment, the engagement mechanism is a clamp 310 that is attached to a ganglion stimulator, which is illustrated in FIG. 18 as being delivery device 10 (only trailing delivery contact 20d shown). Clamp 310 has a spring-loaded mechanism, for example, that allows clamp 310 to move from an open position, as illustrated in FIG. 18A, to a closed position, as illustrated in FIG. 18B. Therefore, when in a loading position of assembly 200 and therefore an open position of clamp 310, trailing delivery contact 20d is able to slide along outer surface of shaft 170.

Once the desired ganglion is located, assembly 200 assumes an operative position and clamp 310 is placed in a closed position and attached trailing delivery element 20d is securely attached to outer surface 180 of shaft 170, as illustrated in FIG. 18C. Trailing delivery contact 20d is then engagably associated with leading delivery contact 20a, as described in detail above, so that delivery device 10 is wrapped around the desired ganglion. Although clamp 310 is illustrated as being substantially C-shaped, clamp 310 may take on any configuration that conforms to the shape of outer surface 180 of shaft 170.

Referring to FIGS. 19 and 20, a ganglion stimulator, which is illustrated as being a probe 210, has an extension 330 extending from distal end 220 that slidably engages outer surface 180 of shaft 170 during a loading position of assembly 200. In this embodiment, engagement mechanism is a clip 320 defining a first pair of arms 321 and a second pair of arms 322. Once the desired ganglion is located, assembly 200 assumes an operative position and clip 320, as illustrated in FIG. 20, is positioned about extension 330 such that extension 330 is gripped between first pair of arms 321 and second pair of arms 322 of clip 320. Although clip 320 is illustrated as being substantially C-shaped and extension 330 is illustrated as being annular, both extension 330 and clip 320 may take on any configuration that conforms to the shape of outer surface 180 of shaft 170.

Referring to FIG. 21, in an alternative embodiment, shaft 170 may define slits 350 along the longitudinal axis thereof to engagably receive extension 330 of probe 210. Alternatively, in embodiments where the ganglion stimulator is sutured in place through the use of surgical threading, shaft 170 may define a series of grooves 360 to retain the surgical threading, as illustrated in FIG. 22. For example, if the ganglion stimulator is delivery device 10, then delivery contacts 20a and 20d may define or have attached thereon suturing rings 120 as illustrated in FIG. 7. Surgical threading may then pass through suturing ring 120 of delivery contact 20a, wrap around the ganglion, enter in and be secured by a groove 360 and pass through suturing ring 120 of delivery contact 260. The surgical threading may then be fastened to secure delivery device 10 around the ganglion. Referring to FIG. 23, shaft 170 may alternatively define a series of apertures 370 along the longitudinal axis thereof and extension 330 of probe 210 may also define a through-hole 375 to receive a securement pin 376. In a loading position of assembly 200, probe 210 is slidably engaged with outer surface 180 of shaft 170 and once reaching the location of the desired ganglion, assembly 200 assumes an operative position and through-hole 375 is brought in registration with the respective aperture 370 of shaft 170 to align probe 210 with the desired ganglion. Securement pin 376 is then inserted into through-hole 375 and respective aperture 370 to secure probe 210 to shaft 170.

Referring to FIG. 24, in an alternative embodiment, engagement mechanism of assembly 200 is a clasp 380 and ganglion stimulator is a delivery structure 240. Clasp 380 has a receiving portion 381 defining an opening 383 and a moveable portion 382 that is slidably insertable through opening 383 into receiving portion 381. In an open position of delivery structure 240, moveable portion 382 rests within receiving portion 381 and as clamping members 242 are brought in mutual confrontation to surround a ganglion, moveable portion 382 is urged through receiving portion 381 towards opening 383. Based on the diameter of delivery structure 240, the length of moveable portion 382 is such that moveable portion 382 does not exit opening 383 when delivery structure 240 is in a fully closed position. In a loading position of assembly 200, clasp 380 is slidably engaged with outer surface 180 of shaft 170. Once the desired ganglion to be stimulated is reached, clamping members 242 are moved into a closed and operative position and moving portion 382 of clasp 380 is urged towards opening 383. Clasp 380 is then secured to shaft 170 by a securement pin 376, or a clip 320 or any other suitable engagement mechanism described above.

The present invention also provides a method of stimulating sympathetic ganglia of the sympathetic nerve chain by positioning shaft 170 adjacent to the sympathetic nerve chain, slidably engaging a first ganglion stimulator with outer surface 180 of shaft 170, the first ganglion stimulator comprising at least one first delivery element 40. The method moreover includes placing the first ganglion stimulator adjacent to a first ganglion, securing the first ganglion stimulator to outer surface 180 of shaft 170, and providing a stimulation signal to the at least one first delivery element 40 to stimulate the first ganglion. The method may further include slidably engaging a second ganglion stimulator with outer surface 180 of shaft 170, the second ganglion stimulator comprising at least one second delivery element 40, placing the second ganglion stimulator adjacent to a second ganglion, securing the second ganglion stimulator to outer surface 180 of shaft 170 and providing a stimulation signal to the at least one second delivery element 40 to stimulate the second ganglion. Although the above-described method has been described with respect to sympathetic ganglia of the sympathetic nerve chain, it is understood that such method may be used with other ganglia as well, particularly ganglia that are serially arranged Notwithstanding the precise nature of the engagement mechanism of assembly 200, in a preferred embodiment, when delivery elements 40 are electrodes, delivery elements 40 of the respective ganglion stimulators are adjustable powerable. For example, the pulsing parameters of delivery elements 40 may be adjusted to initiate, stop, increase, or decrease the pole combinations, energy, amplitude, pulse width, waveform shape, frequency, and/or voltage or any other pulsing parameter known to one of skill in the art to adjust the degree of stimulation delivered thereby. In a preferred embodiment, each delivery element 40 of each ganglion stimulator is selectively powerable such that the pulsing parameters of a delivery element 40 can be adjusted independent of the pulsing parameters of another delivery element 40 of either the same ganglion stimulator or a different ganglion stimulator. In the case of stimulating serially-arranged ganglia such as the ganglia of the sympathetic nerve chain, such selective powerability permits different ganglia of the sympathetic nerve chain to receive different characteristics of stimulation depending on the particular stimulation effects desired to be imparted on the specific ganglion. Methods of selectively powering and steering electrical stimulation are described in U.S. Pat. No. 5,713,922, which is incorporated by reference herein.

A delivery device 10 or stimulation delivery assembly 200 according to the present invention may include or be incorporated with other components useful in identifying, monitoring, or affecting a specific ganglion or ganglia or a particular physiological condition associated with the specific ganglion or ganglia. For example, such a system could include a component for lesioning and temperature monitoring, and/or a component that has a fiberoptic monitor which allows telemetric intracranial monitoring capabilities, and/or a microelectrode recording component, and/or a sensing component to incorporate a feedback mechanism to assist in determining whether the delivery contacts 20 should be adjusted or relocated to a different ganglion. If an assembly 200 according to the present invention is utilized, the above-mentioned components could be incorporated in shaft 180.

With respect to a sensing component according to the present invention, a sensor can be used with a closed-loop feedback system in order to automatically determine the level of stimulation necessary to provide the desired therapy. The sensor may be implanted into a portion of a patient's body suitable for detecting characteristics, symptoms or attributes of the condition or disorder being treated such as electrical brain activity, cerebral blood flow, and/or vital signs or other chemical and electrical activity of the body. Sensors suitable for use in a system according to the present invention include, for example, those disclosed in U.S. Pat. No. 5,711,316, which is incorporated by reference herein.

Furthermore, a stimulation device 10 or assembly 200 according to the present invention may also include or be incorporated with a navigation system that provides the exact position/orientation of device 10 or assembly 200 within the nervous system after device 10 or assembly 200 has been deployed. Preferably, when assembly 200 is utilized such a navigation system is incorporated in shaft 170. For example, if device 10 or assembly 200 has a circular cross-section, the navigation system would provide the compass direction (i.e. degree) device 10 or assembly 200 is positioned relative to a reference point in the nervous system therefore assisting in the determination of where to place device 10 or the ganglion stimulators of assembly 200. Preferably the navigation system would incorporate some type of marker that is integral with device 10 or assembly 200 that would show up under computer tomography (CT) or magnetic resonance imaging (MRI) scanning techniques. According, the scans could be printed and fed into a computer having navigational software and a three-dimensional atlas of the patient's sympathetic nerve chain to model approximately where all the devices 10 or ganglion stimulators of assemblies 200 are positioned. The software may then be capable of providing instructions on where best to position device 10 or the ganglion stimulators of assembly 200 or which delivery elements 40 to activate.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

We claim:

1. A delivery device for stimulating a ganglion of the nervous system, the device comprising:
   a first series of flexibly connected delivery contacts, wherein a leading delivery contact of the first series of flexibly connected delivery contacts is engagably associated with a trailing delivery contact of the first series of flexibly connected delivery contacts in an operative position of the delivery device; and
   a second series of flexibly connected delivery contacts flexibly connected to the first series of flexibly connected delivery contacts, wherein a leading delivery contact of the second series of flexibly connected delivery contacts is engagably associated with a trailing delivery contact of the second series of flexibly connected delivery contacts in an operative position of the delivery device, wherein the delivery device maintains a substantially ovoid configuration when in an operative position; and
   a third series of flexibly connected delivery contacts located between and connected to both the first series of flexibly connected delivery contacts and the second series of flexibly connected delivery contacts, wherein a leading delivery contact of the third series of flexibly connected delivery contacts is engagably associated with a trailing delivery contact of the third series of flexibly connected delivery contacts in an operative position of the delivery device;

wherein the engagable association of the leading delivery contact and the trailing delivery contact for each of the series of flexibly connected delivery contacts is independent of the engagable association of the leading delivery contact and the trailing delivery contact of any other series of flexibly connected delivery contacts;

wherein the first series of flexibly connected delivery contacts has a first diameter, the second series of flexibly connected delivery contacts has a second diameter, and the third series of flexibly connected delivery contacts has a third diameter, the third diameter being greater than the first diameter and the third diameter being greater than the second diameter in an operative position of the device.

2. The device of claim 1, wherein the first series of flexibly connected delivery contacts are arranged in a concave configuration.

3. The device of claim 1, wherein the second series of flexibly connected delivery contacts are arranged in a convex configuration.

4. The device of claim 1, wherein the first series of flexibly connected delivery contacts comprises four delivery contacts, the second series of flexibly connected delivery contacts comprises four delivery contacts and the third series of flexibly connected delivery contacts comprises four delivery contacts.

5. The device of claim 1, wherein each of the first series of flexibly connected delivery contacts comprises an electrode and each of the second series of flexibly connected delivery contacts comprises an electrode.

6. The device of claim 1, wherein each of the first series of flexibly connected delivery contacts comprises a drug port and each of the second series of flexibly connected delivery contacts comprises a drug port.

7. The device of claim 1, wherein each of the first series of flexibly connected delivery contacts is insertable into a ganglion and each of the second series of flexibly connected delivery contacts is insertable in a ganglion.

8. The device of claim 1, wherein each of the first and second series of flexibly connected delivery contacts has a trapezoidal configuration.

9. The device of claim 1, wherein each of the first and second series of flexibly connected delivery contacts has an inner ganglion-facing surface and an outer surface, each of the inner ganglion-facing surfaces of each of the first and second series of flexible connected electrical delivery contacts having a concave configuration.

10. An assembly for stimulating ganglia comprising the device of claim 1 and further comprising an axially elongated shaft that is slidably engagable with the device of claim 1.

11. The device of claim 1, wherein the ganglion is a sympathetic ganglion of a sympathetic nerve chain.

12. An assembly for stimulating a ganglia comprising:
an axially elongated shaft having an inner surface and an outer surface;
a first probe including at least one delivery element disposed thereon, the first probe having a distal end and a proximal end, the distal end of the first probe slidably engagable with the outer surface of the shaft such that the first probe can be repositioned on the shaft, the proximal end of the first probe having one or more prongs for insertion in a ganglion; and
a second probe including at least one delivery element disposed thereon, the second probe having a distal end and a proximal end, the distal end of the second probe slidably engagable with the outer surface of the shaft such that the second probe can be repositioned on the shaft, the proximal end of the second probe having one or more prongs for insertion in a ganglion, wherein in an operative position the distal end of the first probe and the distal end of the second probe are securedly attached to the outer surface of the shaft.

13. The assembly of claim 12, further comprising a limit stop detachably engaged with the outer surface of the shaft.

14. The device of claim 12, wherein the first probe has two prongs and the second probe has two prongs.

15. The assembly of claim 12, wherein the ganglia is sympathetic ganglia.

16. An assembly for stimulating ganglia comprising:
an axially elongated shaft having an inner surface and an outer surface;
a first terminal member including at least one delivery element disposed thereon, the first terminal member having a distal end and a proximal end, the distal end of the first terminal member slidably engagable with the outer surface of the shaft such that the first terminal member can be repositioned on the shaft, the proximal end of the first terminal member having a generally concave configuration and adjacently positionable to a ganglion; and
a second terminal member including at least one delivery element disposed thereon, the terminal member having a distal end and a proximal end, the distal end of the second terminal member slidably engagable with the outer surface of the shaft such that the second terminal member can be repositioned on the shaft, the proximal end of the second terminal member having a generally concave configuration and adjacently positionable to a ganglion, wherein in an operative position the distal end of the first terminal member and the distal end of the second terminal member are securedly attached to the outer surface of the shaft.

17. The assembly of claim 16, further comprising a limit stop detachably engaged with the outer surface of the shaft.

18. The assembly of claim 16, wherein the ganglia are sympathetic ganglia.

19. An assembly for stimulating ganglia comprising:
an axially elongated shaft having an inner surface and an outer surface;
a first delivery structure slidably engagable with the outer surface of the shaft such that the first delivery structure can be repositioned on the shaft, the first delivery structure comprising a first pair of connected clamping members, each of the first pair of connected clamping members having an outer wall and an inner concave wall, each of the inner concave walls of each of the first pair of connected clamping members having at least one delivery element disposed thereon; and
a second delivery structure slidably engagable with the outer surface of the shaft such that the second delivery structure can be repositioned on the shaft, the second delivery structure comprising a second pair of connected clamping members, each of the second pair of connected clamping members having an outer wall and an inner concave wall, each of the inner concave walls of each of the second pair of connected clamping members having at least one delivery element disposed thereon, wherein in an operative position the first and second delivery structures are securely attached to the outer surface of the shaft.

20. The assembly of claim 19, further comprising a limit stop detachably engaged with the outer surface of the shaft.

21. The assembly of claim 19, wherein the ganglia are sympathetic ganglia.

22. The assembly of claim 19, wherein the first pair of connected clamping members are hingedly connected to each other and the second pair of connected clamping members are hingedly connected to each other.

\* \* \* \* \*